United States Patent [19]
Bradley

[11] Patent Number: 6,010,508
[45] Date of Patent: Jan. 4, 2000

[54] AUTOMATIC IMPACT DEVICE

[76] Inventor: Gary W. Bradley, 795 Park La. West, Santa Barbara, Calif. 93108

[21] Appl. No.: 09/181,387

[22] Filed: Oct. 27, 1998

Related U.S. Application Data

[63] Continuation-in-part of application No. 08/958,773, Oct. 27, 1997, Pat. No. 5,827,290, which is a continuation-in-part of application No. 08/735,185, Oct. 25, 1996, Pat. No. 5,735, 855.

[51] Int. Cl.$^7$ ........................................................ A61F 5/00
[52] U.S. Cl. .................................. 606/86; 606/89; 606/92
[58] Field of Search .................................. 606/79, 80, 81, 606/83, 84, 85, 86, 92

[56] References Cited

U.S. PATENT DOCUMENTS

| | | |
|---|---|---|
| 5,490,683 | 2/1996 | Mickel et al. .............................. 606/79 |
| 5,569,256 | 10/1996 | Vaughn et al. .............................. 606/80 |

*Primary Examiner*—Michael Buiz
*Assistant Examiner*—Daphna Shai
*Attorney, Agent, or Firm*—Carol D. Titus; James J. Leary

[57] ABSTRACT

An impact tool useful for performing a number of different surgical and industrial functions is provided. The invented tool can perform such surgical functions as freeing cement, implanting pins, and setting guides and industrial functions such as installing various fasteners. The tool comprises a body having a quick disconnect assembly coupled to a second end for quickly attaching and detaching different desired surgical and industrial implements to the tool. The quick disconnect assembly communicates with an impact inducing assembly is retained in a channel in the body. The impact inducing assembly causes an implement retained in the quick disconnect assembly to deliver an impact with a calibrated force to a desired object. The orientation of the components of the impact inducing assembly can be inverted so that the tool is actuated to apply an instantaneous extraction force to the desired fastener or surgical aid. In the alternative embodiment the user draws the tool away from an object secured to the quick disconnect assembly until the impact inducing assembly disengages the quick disconnect assembly to impel the implement along the channel for delivering an instantaneous extraction force to the desired object, for at least partially withdrawing a portion of the object from a surface in which the object is imbedded. An antirotation assembly may be provided to determine and maintain a desired orientation of various implements coupled to the quick disconnect assembly, when the implement is obscured from the user's view.

18 Claims, 4 Drawing Sheets

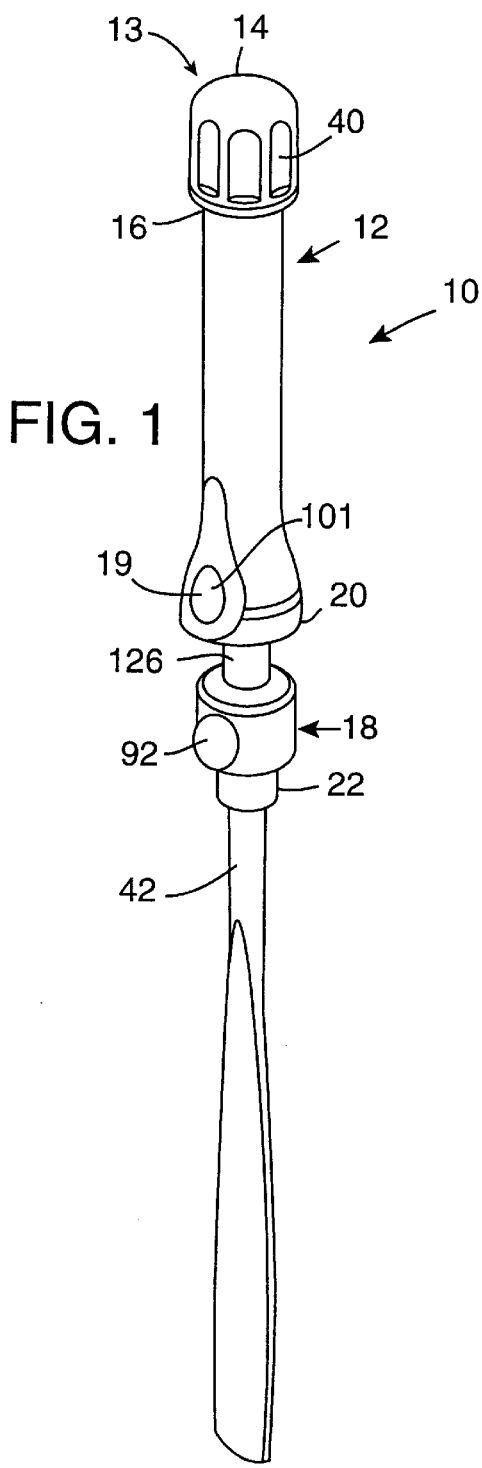
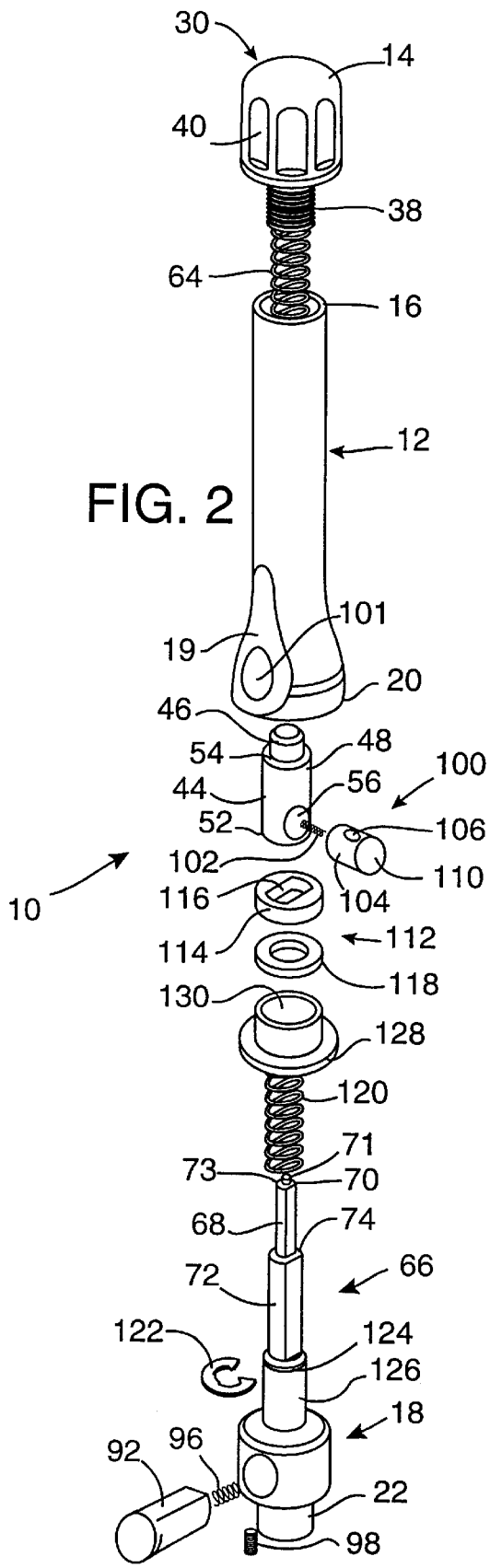

AUTOMATIC IMPACT DEVICE

This application is a continuation-in-part of application Ser. No. 08/958,773, filed Oct. 27, 1997, now U.S. Pat. No. 5,827,290, the specification of which are hereby incorporated by reference in its entirety, which is a continuation-in-part of application Ser. No. 08/735,185, filed Oct. 25, 1996, now U.S. Pat. No. 5,735,855.

BACKGROUND OF THE INVENTION

1. Field of the Invention

The present invention relates generally to impact devices, and more particularly, to an impact tool for performing different surgical functions in various different surgical procedures and for performing various different industrial functions.

2. Description of Related Art

As can well be appreciated, the instruments a surgeon uses while performing a surgical procedure are of the utmost importance. Ease of use, reliability, and operating precision are important features of these instruments.

When performing surgical procedures, such as orthopedic procedures, the surgeon often uses several instruments that each perform a different function during the procedure. In a procedure, such as a hip replacement operation for example, the surgeon first typically removes the head of the femur. Once the head of the femur is removed, the surgeon may use an osteotome for hollowing out the medullary canal of the femur, to form a cavity in the bone, to prepare the femur for receiving the replacement femoral component. Once the cavity is suitably prepared, an appropriate medical adhesive, such as a liquid acrylic cement, is disposed in the cavity, and the replacement femoral component is disposed in the cavity to affix the component to the femur.

If the purpose of the hip replacement operation is to supplant a failed replacement, the surgeon may further use a gouge and chisel along with the osteotome. The gouge and other instruments are used to remove residual adhesive from the cavity, due to the preceding hip replacement, to prepare the cavity for the new femoral component.

Additionally, these and other instruments are used for a number of different purposes. For example, another use of chisels is to remove bone spurs. Another instrument that is used by orthopedic surgeons is a surgical pin inserter. The pin inserter may be used by the surgeon for inserting surgical pins that facilitate the fixation of fractured bones. The pin inserter is also used to temporarily couple guides to various bones, such as securing guides to the tibia or femur during a knee replacement procedure. Also, when a hip replacement operation is supplanting a failed replacement, guides can be employed when affixing the new femoral component to the femur.

Common to each of these instruments, is that an instantaneous force has to be applied to the instrument, to cause the instrument to function. The force causes the instrument to deliver an instantaneous impact to a desired object, such as a portion of bone or a pin, for performing the desired function, such as cutting bone or inserting the pin. Known medical methods usually require the surgeon to strike the instrument with an appropriate device, such as a hammer, to cause the instrument to momentarily impact the object.

As can be appreciated, it is substantially difficult to manually strike the instrument with a consistent, optimal impact force, which can result in either an excessive or insufficient impact force being applied to the object by the instrument. To inhibit an excessive force from being applied to the object, the surgeon often repeatedly strikes the instrument with a force that is somewhat less than sufficient, which often results in the procedure taking longer than is necessary. A further disadvantage of using a hammer to induce an impact, is that the surgeon must operate both the hammer and instrument. Thus, the surgeon is not afforded one-handed operation of the instrument.

To increase the speed with which the desired implement delivers successive impacts, a pneumatic power source may be coupled to the instrument. However, a disadvantage of using pneumatic power, is that the instrument rapidly and repeatedly impacts the object, causing the instrument to be somewhat difficult to control.

It therefore would be advantageous to provide a means for enabling an instrument to deliver an impact to an object with an optimal force and in a controllable manner.

Additionally, during performance of any of the above discussed surgical procedures, or any one of several well known procedures, it is often necessary to affix and remove surgical aids, such as the surgical pins, that are temporarily secured to a patient's bones for securing guides to the bones to facilitate performance of the procedure. Also, sometime after performing any one of the above discussed surgical procedures, or any one of several well known procedures, it is often necessary to remove surgical aids, such as the surgical pins, that are temporarily secured to a patient's bones to facilitate fixation of the fractured bones.

However, common to installing these surgical aids, it is often difficult to remove these aids and other devices, particularly in a controlled and efficient manner. It therefore would be advantageous to provide a means for facilitating removal of these and other devices that are temporarily affixed to a patient's bones, or other portions of the patient's anatomy.

Punch tools are well known in the prior art. Punches are used for a number of different applications, such as making shallow indentations in metal work or breaking glass. For example, a center punch can be used to make a shallow indentation in a portion of sheet metal, to prepare the metal for accurately drilling openings therethrough at predetermined positions. Punches are additionally used by emergency personnel to break vehicle windows and other appropriate purposes.

A center punch tool typically comprises a hollow steel body with a steel tip that extends through an end of the body. The tip is usually configured with a conical end portion for impacting a desired surface. A loaded spring is retained in the body, with release means coupling the spring to the tip. The body may have a handle coupled to the spring, to adjust for light or heavy strokes of the tip.

In use, the conical end of the tip is pressed against a surface to be impacted by the center punch. As the tip is pressed against the surface, the tip is forced into the body. As the tip is pushed into the body, upon reaching a determined point in the body, the release means causes the spring to instantaneously propel the end of the tip into the surface, to momentarily impact the surface, thus indenting or breaking the surface struck by the tip.

A disadvantage of known punch tools is that they are not well suited for a number of different industrial uses. A further disadvantage of known punch tools is that they are not configured with means for coupling different implements thereto.

There, therefore, exists a need for an impact tool for performing different surgical and industrial functions that delivers an impact to an object with an optimal force and in a controllable manner and is capable of applying an instantaneous extraction force to an object to effect removal of the object from a surface in which at least a portion of the object is imbedded.

OBJECTS OF THE INVENTION

It is therefore an object of the present invention to provide an improved impact tool;

It is another object of the present invention to provide an improved impact tool for performing different surgical functions;

It is a further object of the present invention to provide an improved impact tool that is well suited for performing a number of different industrial functions;

It is still another object of the present invention to provide an improved impact tool that delivers an impact to an object with an optimal force and in a controllable manner;

It is a further object of the present invention to provide an improved impact tool that is coupleable to different objects and is actuated for instantaneous extraction of the objects from a surface in which at least a portion of the object is imbedded;

It is yet a further object of the present invention to provide an improved impact tool that affords one-handed operation thereof; and It is another object of the present invention to provide an impact tool that includes a quick disconnect fitting for alternately quickly connecting and disconnecting a number of different implements thereto.

SUMMARY OF THE INVENTION

These and other objects and advantages of the present invention are achieved by providing an improved impact tool for performing a number of different surgical and industrial functions. The improved impact tool of the present invention is useful for performing a number of different functions in various surgical procedures, such as hip replacement procedures for example. Several different surgical implements can alternately be coupled to the invented tool during surgical procedures, to perform such surgical functions as freeing and removing cement, inserting pins, accurately setting guides, and implanting surgical staples. Some of these surgical implements include an acetabular adjuster, a surgical pin inserter, a surgical stapler, a bone chisel, an osteotome, and a gouge.

Additionally, the improved impact tool of the present invention may be utilized in different industrial applications wherever an impact force is desired, such as the several different impact forces associated with construction, for instance. The impact tool of the present invention can be configured into several different dimensions that render the tool suitable for delivering an impact of sufficient force to various fasteners, such as nails or other similar fasteners, to drive the fastener into a surface comprising wood, sheetrock or drywall, or metal alloy surfaces among others.

Further, the tool of the present invention includes means for effecting removal of various surgical aids and other devices, along with various industrial fasteners. As with installing surgical aids and industrial fasteners, along with other devices, it is often difficult to remove these devices, particularly in a controlled and efficient manner. The impact tool of the present invention is capable of applying an instantaneous extraction force to an object to effect removal of the object from a surface in which at least a portion of the object is imbedded.

For example, the invented impact tool is coupleable to different implements adapted to be secured to a surgical aid, such as a pin. The invented tool then is actuated for applying an instantaneous extraction force to the pin, to effect removal of the pin from a bone in which at least a portion of the pin is imbedded. The tool can be repeatedly actuated until the pin is entirely removed from the bone. Similarly, the invented impact tool can be secured to industrial fasteners for removing the fasteners from a surface that the fasteners are imbedded.

In the preferred embodiment of the present invention, the improved impact tool comprises a handle portion or body having an impact force calibrating means coupled to a first end thereof and a quick disconnect assembly secured in a second end. The quick disconnect assembly comprises a chuck having a rod that extends into a channel in the body, for coupling the quick disconnect assembly to the body, and a jaw assembly. The jaw assembly includes a quick-release means for quickly attaching and detaching different desired surgical and industrial implements to the tool.

The channel extends through the body and has a first region that extends from the first end of the body to a midpoint that is intermediate the first and second ends of the body, and a second region that extends from the second end to the midpoint. The channel further includes a transition region that extends about its midpoint.

An impact inducing assembly is provided for causing an implement coupled to the quick disconnect assembly to deliver an impact to a desired object, such as the above discussed surgical aids and industrial fasteners, with an impact force calibrated by the calibrating means, and without the use of external means, such as a hammer. The impact inducing assembly is retained in the channel and comprises a piston slidably retained in the first region of the channel, a main spring interposed between the piston and calibrating means, and coupled thereto, and an actuation mechanism configured to releasably engage the rod.

In the preferred embodiment, the actuation mechanism comprises an actuation spring secured in an inner surface of the piston and a trigger member slidably retained in a hole through a wall thereof and coupled to the actuation spring. The trigger has an opening disposed therethrough that is dimensioned to allow the rod to extend through the trigger and into the piston. The actuation spring biases the trigger outwardly, so that the trigger projects outwardly from the piston to contact the transition region of the channel.

Optionally, a trigger means may be disposed through the body and coupled thereto, for contacting the actuation mechanism. The trigger means may be positioned on the body, between the second end and midpoint, depending upon such factors as the intended application of the invented tool, for example. The trigger means enables the implement to deliver an impact, without the user having to exert substantial pressure on the object, to initiate the impact. Thus, the trigger means enables the tool to be used in applications where only a slight impact force is desired, such as dentistry.

An antirotation assembly may be provided to prevent the implement from rotating relative to the body, while the rod travels along the channel. Preferably, the antirotation assembly includes an adjustable member secured in the second region of the channel. The adjustable member has an aperture disposed therethrough configured complementary to the end section and a mid section of the rod, for allowing the rod to pass therethrough, while preventing the rod from rotating about in the channel. Additionally, a depression may be formed in the periphery of the body, preferably proximal to the second end thereof. The antirotation assembly and depression coact to enable a user to determine and maintain a desired orientation of various implements coupled to the quick disconnect assembly, when the implement is obscured from the user's view.

Return means are provided for causing the rod to be engaged by the actuation mechanism for returning the impact inducing assembly to an initial position, thus affording one-handed operation of the invented tool. In the preferred embodiment, the return means comprises a return spring interposed between the adjustable member and the second end of the body and coupled to the rod of the quick disconnect assembly's chuck. The return spring biases the rod toward the second end of the body, causing the end of the rod to be engaged by the trigger, thus coupling the rod to the piston.

In use, the impact inducing means is in the initial position, wherein the main spring exerts force on the piston to retain the actuation mechanism in the second region of the channel, to prevent the impact inducing means from causing the implement to deliver an impact. A connecting portion of a selected surgical or industrial implement is coupled to the quick disconnect assembly. The user grasps the tool and may place their thumb, or one of their other fingers, for maintaining the orientation of the implement if necessary. As the user applies pressure to the implement with the tool, the piston is urged toward the first end of the body to compress the main spring. The piston is urged toward the first end until a head of the trigger contacts the transition region of the channel.

As the head of the trigger contacts the transition region, the trigger is pushed into the hole for compressing the actuation spring, to disengage an end section of the chuck's rod from the trigger for causing the inducing means to deliver an impact to the desired object. The implement is caused to deliver an impact, due to the rod passing into the piston, which causes the main spring to propel the piston along the rod until the piston strikes a shoulder thereof. Once the piston strikes the shoulder, the piston and rod are propelled instantaneously along the second region of the channel until the implement impacts the object. As the rod is propelled along the second region, the antirotation assembly prevents the rod from rotating about in the channel, thus affording one-handed operation of the invention.

After the implement impacts the object, the piston is drawn toward the first end of the body by the calibration means with the return means retaining the rod proximal to the second end, for withdrawing the rod out of the cavity. The rod is drawn out of the piston until a portion of the end section passes into the opening in the trigger. The actuation spring biases the trigger outwardly, such that the bottom edge of the trigger is pressed against the end section to engage the rod and return the impact inducing means to the initial position. This enables the tool of the present invention to cause the implement to deliver subsequent impacts to the object with a consistent and optimal impact force controlled by the calibration means.

Alternatively, the orientation of the components of the impact inducing assembly, along with the orientation of the transition region of the channel, can essentially be inverted so that invented tool can be actuated to apply an instantaneous extraction force to the desired fastener or surgical aid. In the alternative embodiment, an implement coupled to the quick disconnect assembly is provided with means for securely attaching the implement to the object, such as the above discussed surgical aids and industrial fasteners. The user then draws the impact tool away from the object until the trigger of the impact inducing assembly contacts the transition region and disengages the end section of the chuck's rod to cause the impact inducing means to impel the implement along the channel for delivering an instantaneous extraction force to the desired object, for at least partially withdrawing a portion of the object from a surface in which the object is imbedded. The user can repeatedly draw the impact tool away from the object until the object is completely removed from the surface if desired.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, in which:

FIG. 1 is a perspective view showing a preferred embodiment of an impact tool for use in surgical procedures of the present invention with a surgical implement coupled thereto;

FIG. 2 is a perspective, exploded view showing the preferred embodiment of the present invention;

DESCRIPTION OF THE PREFERRED EMBODIMENTS

Figure 3:
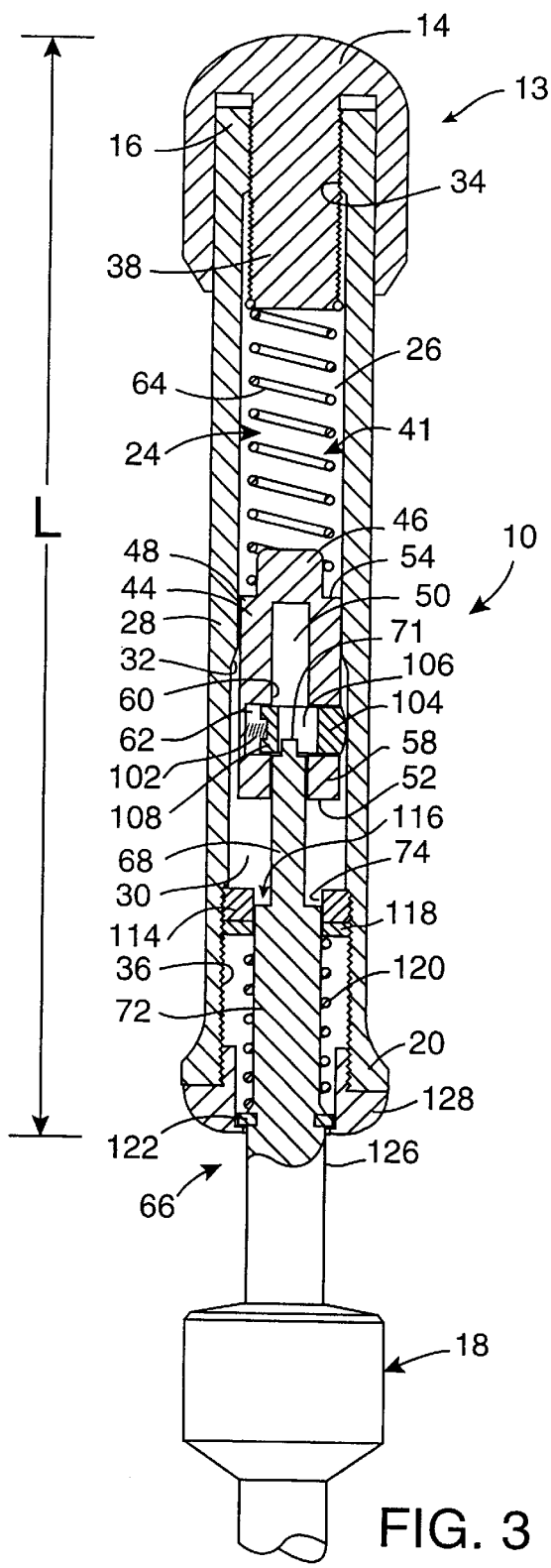
FIG. 3 is a cross-sectional view of the preferred embodiment showing components thereof.

The following description is provided to enable any person skilled in the art to make and use the invention and sets forth the best modes presently contemplated by the inventor of carrying out the invention. Various modifications, however, will remain readily apparent to those skilled in the art, since the generic principles of the present invention have been defined herein.

Referring now to FIG. 1 and FIG. 2 of the drawings, there is shown generally at 10, a preferred embodiment of an impact tool for use in a number of different surgical and industrial functions, constructed according to the principles of the present invention. The tool 10 is preferably fabricated from known light, strong, and rigid biocompatible metal alloys, or polymeric composites, or other known suitable materials. In the present invention, the invented tool 10 is preferably fabricated from suitable metal alloys, such as a stainless steel alloy sold under the trade name Stellite, and titanium alloys. The invented tool 10 may also be fabricated from cobalt alloys sold under the trade names Elgiloy and Carpenter MP35.

The impact tool 10 of the present invention is useful for performing a number of different functions in various surgical procedures, such as hip replacement procedures. Several different surgical implements can alternately be coupled to the invented tool during surgical procedures, to perform such surgical functions as freeing and removing cement, inserting pins, accurately setting guides, and implanting surgical staples. Some of these surgical implements include an acetabular adjuster, a surgical pin inserter, a surgical stapler, a bone chisel, an osteotome, and a gouge.

Additionally, the impact tool 10 may be utilized in different industrial applications wherever an impact force is desired, such as the several different impact forces associated with construction, for instance. The tool 10 can be configured into several different dimensions that render the tool 10 suitable for delivering an impact of sufficient force to various fasteners, such as nails or other similar fasteners, to drive the fastener into a surface comprising wood, sheetrock or drywall, or metal alloy surfaces, among others.

Further, the tool 10 of the present invention includes means for effecting removal of various surgical aids and other devices, along with various industrial fasteners. As with installing surgical aids and industrial fasteners, along with other devices, it is often difficult to remove these devices, particularly in a controlled and efficient manner. The impact tool 10 of the present invention is capable of applying an instantaneous extraction force to an object to effect removal of the object from a surface in which at least a portion of the object is imbedded. For example, the invented impact tool 10 is coupleable to different implements adapted to be secured to a surgical aid, such as a pin. The tool 10 then is actuated for applying an instantaneous extraction force to the pin, to effect removal of the pin from a bone in which at east a portion of the pin is imbedded. The tool 10 can be repeatedly actuated until the pin is entirely removed from the bone. In a similar fashion, the invented impact tool 10 can be secured to industrial fasteners for removing the fasteners from a surface that the fasteners are imbedded.

Referring still to FIG. 1 and FIG. 2, the invented tool 10 comprises a handle portion or body 12 having an impact force calibrating means 13 coupled to a first end 16 thereof and a quick disconnect assembly 18 secured in a second end 20. The body 12 optionally may be provided with an ovular depression 19 formed in the periphery thereof, preferably proximal to the second end 20. The depression 19 is provided for placement of the user's thumb to enhance grasping of the body 12, for preventing the tool 10 from inadvertently moving in a user's hand while the tool 10 is in use. Additionally, the depression 19 enables a user to determine and maintain a desired orientation of various implements coupled to the quick disconnect assembly 18, when the implement is obscured from the user's view.

Referring now to FIGS. 1–4, in the preferred embodiment of the invented tool 10, the body 12 is elongated and has a channel 24 that extends therethrough and parallel to a longitudinal axis L of the body 12. In the preferred embodiment, the channel 24 has a first region 26 of a first diameter extending from the first end 16 to a midpoint 28 that is intermediate the first and second ends 16, 20, a second region 30 having a diameter greater than the first region 26 extending from the second end 20 to the midpoint 28, and a conical ramp 32 formed about the midpoint 28. The conical ramp 32 provides a smooth transition region between the first and second regions 26, 30 of the channel 24. Further, a portion 34 of the first region 26 of the channel 24 may be threaded for receiving the calibrating means 13, and a portion 36 of the second region 30 of the channel 24 may be threaded for coupling the quick disconnect assembly 18 to the body 12.

The calibrating means 13 preferably comprises a conical knob 14 having a screw 38 made integral therewith. The screw 38 is configured to mate with the threaded portion 34 of the channel's first region 26 for adjustably coupling the knob 14 to the body 12. The knob 14 may be provided with a multiplicity of spatially positioned elongated furrows 40 formed in the periphery thereof. The furrows 40 are provided to enhance gripping of the knob 14, when adjusting the knob 14 to calibrate and adjust the impact force to be delivered by the tool 10.

Figure 4:
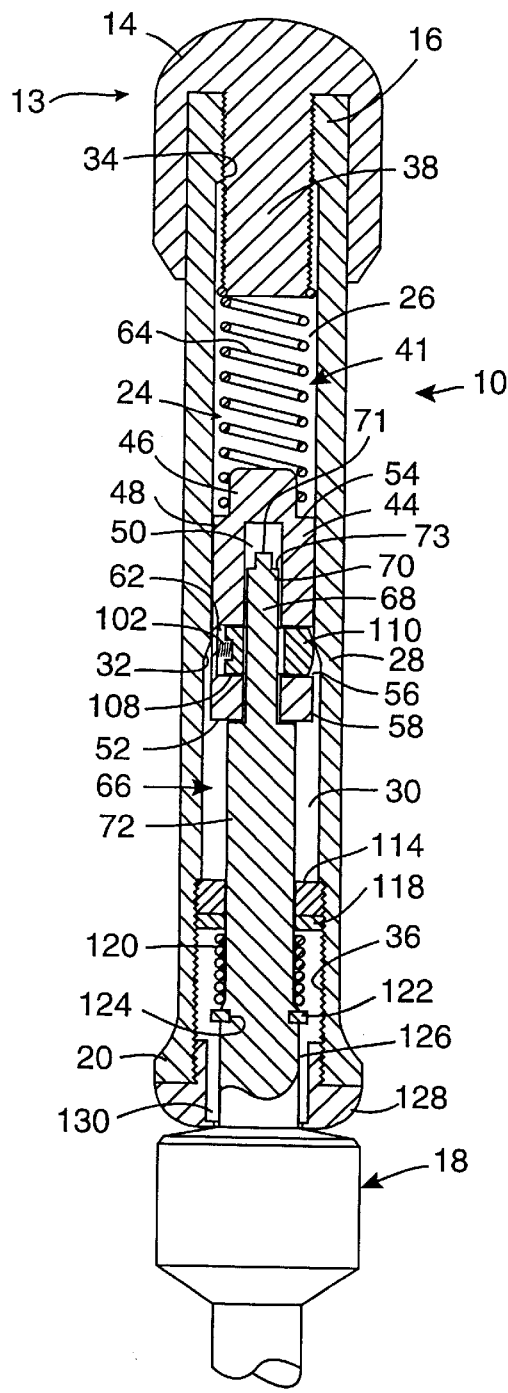
FIG. 4 is a cross-sectional view of the preferred embodiment showing components thereof in an initial position.

Referring now to FIGS. 2–4 of the drawing figures, the preferred embodiment of the invented tool 10 includes an impact inducing assembly, shown generally at 41, retained in the channel 24. The impact inducing assembly 41 is provided to cause a surgical implement 42 retained in the quick disconnect assembly 18 to deliver an impact to a desired object, with an impact force calibrated by the calibrating means 13. In the preferred embodiment, the impact inducing assembly 41 comprises a hollow piston 44 slidably retained in the channel 24. The piston 44 has a head 46 formed on a first end 48, and an elongated cavity 50 disposed through a second end 52 thereof. The head 46 of the piston 44 has a diameter less than the piston 44, to form a flange 54 about the first end 48. A hole 56 is formed through a wall 58 of the piston 44 proximal to the second end 52. The hole 56 extends perpendicular to the cavity 50 and into an inner surface 60 thereof, such that a depression 62 is formed in the inner surface 60 of the piston 44, aligned with the hole 56.

The impact inducing assembly 41 further includes a main spring 64 that is interposed between the piston 44 and calibrating means 13. The main spring 64 is configured to frictionally, engage the head 46 of the piston 44 and to couple to the screw 38 of the knob 14. In use, as the knob 14 is rotated clockwise, the screw 38 extends further into the first region 26 of the channel 24 to increasingly bias the main spring 64 against the head 46, for increasing the impact force generated by the impact inducing assembly 41.

Referring now to the drawing figures, the quick disconnect assembly 18 includes a chuck 21 having a rod 66 configured to extend into the channel 24, for coupling the quick disconnect assembly 18 to the body 12. As shown in FIGS. 2–4, the rod 66 has an end section 68 that extends from an end 70 thereof to a mid section 72. The end section 68 is dimensioned to extend into the cavity 50, with the mid section 72 having a diameter greater than the diameter of the end section 68, for forming a shoulder 74 about the juncture of the end and mid sections 68, 72.

Preferably, each of the end and mid sections 68, 72 are substantially cylindrical with chordal sides to prevent the rod 66 from rotating about the longitudinal axis L of the body, when the rod 66 is traveling along the second region 30 of the channel 24 (discussed hereafter). Additionally, a boss 71 is formed on the end 70 of the rod 66 to form a flange 73.

Figure 5A:
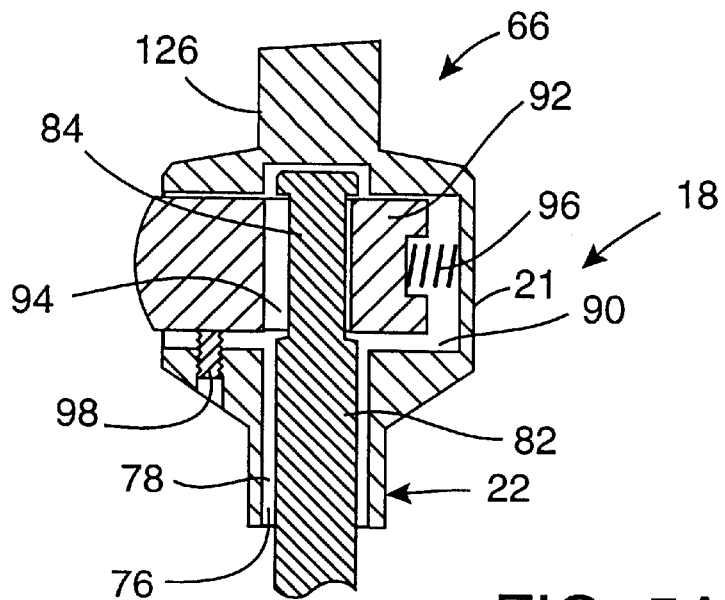
FIGS. 5A and 5B are a cross-sectional views of a chuck assembly of the preferred embodiment of the present invention.
Figure 5B:
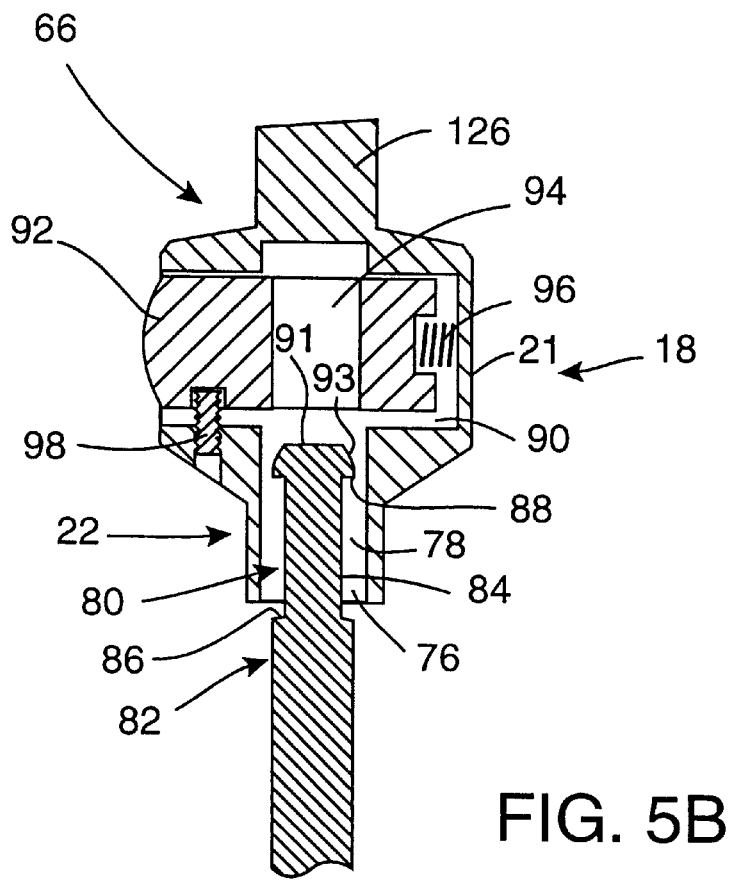

Referring now to FIG. 2 and FIGS. 5A–5B, the quick disconnect assembly 18 is provided with a quick-release jaw means 22 for quickly attaching and detaching different desired implements, such as the above discussed surgical and industrial implements, to the tool 10. In the preferred embodiment, the quick-release jaw means 22 is integrally formed with the chuck 21 and diametrically opposed to the rod 66. The jaw means 22 includes a cylindrical mouth 76 that provides access to an elongated opening 78 in the quick disconnect assembly 18. The opening 78 is configured to receive a connecting portion 80 of an end region 82 of the implement 42 for coupling the implement 42 to the assembly 18.

In the present invention, the connecting portion 80 of the implement 42 comprises a narrowed portion 84 extending between an anterior shoulder 86 and a posterior shoulder 88. An end 91 of the connecting portion 80 may be configured with chamfered edges 93 so that the implement 42 can be coupled to the quick disconnect assembly 18 without having to depress a push-button 92 thereof (discussed hereinafter).

While the only implement 42 shown is a curved osteotome, it is to be understood that any one of several different surgical and industrial implements can alternately be coupled to the quick disconnect assembly 18, providing that they are configured with an appropriate connecting portion, or other suitable means, for coupling the desired implement to the tool 10. Such appropriate implements include an acetabular adjuster, a surgical pin inserter, a surgical stapler, a bone chisel, an osteotome, and a gouge, for example. Further, the improved impact tool 10 of the present invention may be utilized in different industrial applications wherever an impact force is desired, such as the several different impact forces associated with construction, for instance.

The impact tool 10 can be configured into several different dimensions, along with the components of the tool 10 that produce the impact force. Thus, the tool 10 37 can be dimensioned for delivering substantially large impacts of sufficient force to various fasteners, such as nails or other similar fasteners, to drive the fastener into relatively hard surfaces comprising wood, sheetrock or drywall, or metal alloy surfaces among others, or a somewhat slight impact force for driving small fasteners into relatively soft surfaces. Further, the calibrating means 13 is provided to enable various dimensioned tools 10 to deliver a substantially wide range of impact forces.

An aperture 90 is disposed through the chuck 21, diametrically opposed to the opening 78 and has the push-button 92 housed therein. The push-button 92 is configured with an orifice 94 to engage the connecting portion 80 of the implement 42, to releasably couple the implement 42 to the tool 10 of the present invention. A small bias spring 96 is secured in the aperture 90 for biasing the push-button 92 outwardly. In use, the push-button 92 is depressed to compress the bias spring 96, for aligning the orifice 94 in the button 92 with the opening 78 in the chuck 18, to allow the connecting portion 80 to pass into the opening 78 and through the orifice 94. Alternatively, as discussed above, the chamfered edges 93 of the end 91 of the connecting portion 80 cause the end 91 to self-align in the aperture 90, as the implement 42 is being coupled to the assembly 18, and to compress the bias spring 96 for coupling the implement 42 to the quick disconnect assembly 18, without having to depress a push-button 92.

Once the connecting portion 80 is sufficiently disposed in the opening 78, wherein the portion 80 is aligned with the orifice 94, the push-button 92 is released by the user or self-releases once the posterior shoulder 88 is beyond the push button 92. When the button 92 is released, the spring 96 biases the button 92 outwardly for engaging the connecting portion 80, to couple the implement 42 to the chuck 21, and thus to the quick disconnect assembly 18. Optionally, a set screw 98 or other suitable means can be disposed through the chuck 21 and adjusted to abut the push-button 92, to prevent the button 92 from inadvertently disengaging the implement 42.

Referring again to FIGS. 2–4, the impact inducing assembly 41 further includes an actuation mechanism, shown generally at 100 in FIG. 2, configured to releasably engage the end section 68 of the rod 66. In the preferred embodiment, the actuation mechanism 100 comprises an actuation spring 102 secured in the depression 62 and a trigger member 104 slidably retained in the hole 56 and coupled to the actuation spring 102. The trigger 104 has an opening 106 disposed therethrough, perpendicular to the cavity 50 to form a bottom edge 108. The opening 106 is dimensioned to allow the end section 68 of the rod 66 to extend through the trigger 104 and into the cavity 50. The actuation spring 102 is provided to bias the trigger 104 outwardly, such that a head 110 thereof normally projects outwardly from the periphery of the piston 44 to contact the transition region 32 of the channel 24.

Optionally, a trigger means may be disposed through the body 12 and coupled thereto, for actuating the actuation mechanism 100. The trigger means may be positioned on the periphery of the body 12, between the second end 20 and midpoint 28, depending upon such factors as the intended application of the present invention 10. For example, a trigger button 101 may be positioned in ovular depression 19, for example, or other suitable locations along the body 12. The trigger button 101 enables the implement 42 to deliver an impact, without the user having to exert substantial pressure on the object, to initiate the impact. Thus, the trigger button 101 enables the tool 10 to be used in applications where only a slight impact force is desired, such as dentistry.

Referring still to FIGS. 2–4 of the drawings, in the preferred embodiment of the present invention 10, an antirotation assembly, shown generally at 112 (in FIG. 2), is provided to prevent the implement 42 from rotating relative to the longitudinal axis L, while the rod 66 travels along the second region 30 of the channel 24. The antirotation assembly 112 includes an adjustable member 114 that is threaded into the threaded portion 36 of the second region 30. The adjustable member 114 has an aperture 116 disposed therethrough configured complementary to the end and mid sections 68, 72 of the rod 66.

Preferably, the aperture 116 disposed through the member 114 is annular with chordal sides for allowing the end and mid sections 68, 72 to pass through the aperture 116, and to provide a slip-fit between the mid section 72 and the adjustable member 114. A locking nut 118 may further be provided to prevent the adjustable member 114 from inadvertently moving along the threaded portion 36 of the channel's second region 30. The antirotation assembly 112 and depression 19 coact to enable a user to determine and maintain a desired orientation of various implements 42 coupled to the quick disconnect assembly 18, when the implement 42 is obscured from the user's view.

Return means are included for causing the rod's end section 68 to be engaged by the actuation mechanism 100 for returning the impact inducing assembly 41 to an initial position (as shown in FIG. 3). The return means comprises a return spring 120 interposed between the adjustable member 114 and the second end 20 of the body 12 and disposed about the rod's mid section 72. A circlip 122 is retained in a groove 124 in the rod 66, formed about the juncture of the mid section 72 and a base section 126 of the rod 66. The circlip 122 and locking nut 118 cooperate to retain the return spring 120 in the second region 30.

Further, an end cap 128 is threadably coupled to the second end 20 of the body 12. The end cap 128 has an annular opening 130 dimensioned to slip-fit the base section 126, while retaining the circlip 122 in the body 12. The return spring 120 presses against the nut 118 and circlip 122, to bias the rod 66 toward the second end 20, causing the boss 71 to be engaged by the actuation mechanism 100.

In use, the impact inducing assembly 41 is in an initial position, wherein the main spring 64 exerts force on the piston 44 to retain the actuation mechanism 100 in the second region 30 of the channel 24, for preventing the impact inducing assembly 41 from causing the implement 42 to deliver an impact. As pressure is applied to the implement 42 by the tool 10, such as when the implement 42 is pressed against a portion of bone (not shown), the piston 44 is urged toward the first region 26 of the channel 24, thus compressing the main spring 64. The piston 44 is urged into the first region 26 until the head 110 of the trigger 104 contacts the transition region 32 of the channel 24.

As the trigger's head 110 the contacts the transition region 32, the trigger 104 is pushed into the hole 56 and compresses the actuation spring 102. The trigger 104 is pushed into the hole 56 until the bottom edge 108 thereof is flush with the inner surface 60 of the piston 44. This causes the boss 71 and flange 73 to be disengaged by the trigger's bottom edge 108, thus releasing the end section 68 of the rod 66, to allow the end section 68 to pass into the cavity 50. The main spring 64 instantaneously propels the piston 44 along the end section 68, until the piston's second end 52 strikes the rod's shoulder 74. The main spring 64 then instantaneously propels the piston 44 and rod 66 outwardly along the channel 24, until the implement 42 impacts the desired object (not shown) with an impact force calibrated by the calibrating means 13. As the rod 66 is propelled along the channel's second region 30, the antirotation assembly 112 prevents the rod 66 from rotating relative to the body's longitudinal axis L.

After the implement 42 impacts the object, the piston 44 is drawn toward the body's first end 16 by the recoil of the main spring 64, since the spring 64 is coupled to the calibrating means 13. The return spring 120 retains the base section 126 of the rod 66 proximal to the body's second end 20, for withdrawing the end section 68 out of the cavity 50. The end section 68 is drawn out of the cavity 50, until the boss 71 passes into the opening 106 in the trigger 104. The actuation spring 102 biases the trigger 104 outwardly, such that the bottom edge 108 engages the boss 71. This enables the tool 10 of the present invention to cause the implement 42 to deliver subsequent impacts to the object with an impact force determined by the calibrating means 13.

The orientation of the components of the invented impact tool 10 that produce an impact can essentially be inverted so that the tool 10 can be actuated to apply an instantaneous extraction force to the desired industrial fastener, surgical aid, etc. The orientation of the components comprising the impact inducing assembly 41, along with the orientation of the transition region 32 of the channel 24, can essentially be inverted so that invented tool 10 can be actuated to apply an instantaneous extraction force to the desired fastener, surgical aid, or other piece. Additionally, the configuration of the rod 66 and piston 44, along with other desired components of the tool 10, may be modified, or other suitable means may be implemented, for securing the rod 66 to a desired component, such as the piston 44, of the impact inducing assembly 41. In the alternative embodiment, when the impact inducing assembly 41 is actuated, the assembly 41 instantaneously draws the quick disconnect assembly's rod 66 into the channel 24 for applying an instantaneous extraction force to the desired object.

Figure 6:
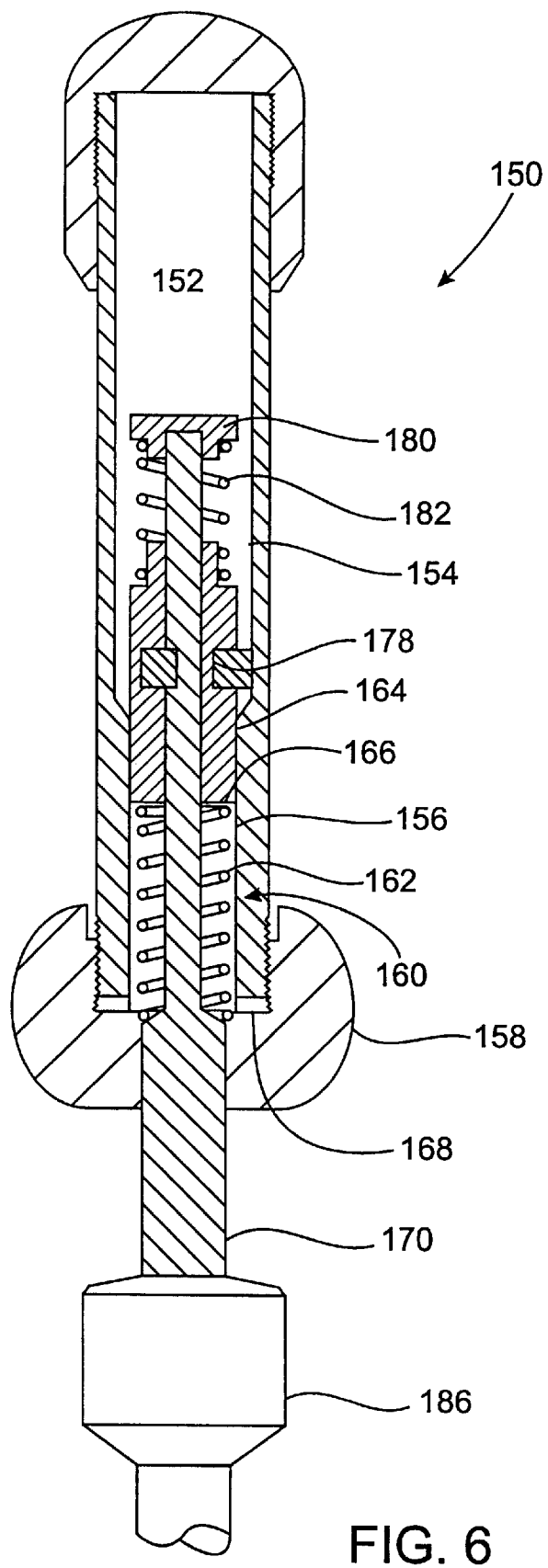
FIGS. 6 is a cross-sectional view of an extraction embodiment of the present invention.

Referring now to FIG. 6, a possible embodiment of the extraction version 150 is shown. The user calibrates the force to be applied to the object being removed by adjusting the calibration knob 158, thereby adjusting the amount of compression preapplied to the spring 162 of the impact inducing assembly 160. One end of the spring 162 is located against the end 166 of a collar 164, and the second end of the spring 162 is located against the shoulder 168 of the calibration knob 158. The collar 164 is located around a rod 170 having an attachment mechanism (not shown) coupled to one end by a quick disconnect assembly 186. During operation, the user engages the grasping implement, such as a vice or clamp, to the object to be drawn from the surface, then pulls the body 172 away from the object, thereby priming the impact inducing assembly 160. As the body 172 moves away from the object, the trigger 174 is urged towards and eventually contacts the transition region 176 of the channel 152. When the trigger 174 moves through the transition region 176, the opening 178 within the trigger 174 aligns with the rod 170, thereby releasing the collar 164. The spring 162 of the impact inducing assembly 160 is released and moves the collar 164 back toward its original position, thereby causing the end of the collar 164 to strike the head 180 of the rod 170. When the collar 164 strikes the rod 170, an impact force is imparted which creates an instantaneous pulling force on the object. If the object has not been fully removed, the user may move the body 172 back towards the object to reset the impact inducing assembly 160. This causes the return spring 182 to realign the trigger 174 of the collar 164 with the depression 184 in the rod 170 and locks the collar 164 and rod 170 to move together as a unit. Once impact inducing assembly 160 is reset, the user may actuate the extraction tool 150 again, if desired. Once the object has been fully removed, the main spring 162 of the impact inducing assembly 160, and the return spring 182 will automatically reset the extraction tool 150 to its original position. Although in the embodiment shown, the springs 162, 182 operate in compression, the system may be designed with tension springs if preferred.

Thus, there has been described an impact tool useful for performing a number of different surgical and industrial functions. The quick disconnect assembly is provided for alternately quickly attaching and detaching different desired surgical and industrial implements to the tool. The orientation of the components of the impact inducing assembly can be inverted so that the tool is actuated to apply an instantaneous extraction force to the object. The antirotation assembly and depression coact to enable a user to determine and maintain a desired orientation of various implements coupled to the quick disconnect assembly, when the implement is obscured from the user's view.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. An impact tool for use with an extraction implement, the impact tool comprising:

a body having a first end, a second end, and an opening extending therethrough, the opening having a first diameter at the first end, a second diameter at the second end, and a transition portion which tapers between said first and second diameters, a calibration knob connected with the second end of the body, a rod having a first end and a second end, the first end of the rod being located within the body, the second end of the rod being configured to connect with the extraction implement, a head extending around the edge of the first end of the rod, a collar located within the body and slidably engaging the rod between the first and second ends thereof and slidably engaging the body, a trigger extending through the collar, an impact spring positioned between the collar and the calibration knob, the impact spring biasing the collar towards the first end of the body, and a return spring positioned between the head of the rod and the collar, the return spring biasing the head of the rod away from the collar, wherein, when the extraction implement is engaged with an object to be pulled and the body of the impact tool is pulled, the collar is moved within the opening of the body between the first and second diameters, causing the trigger to move between an engaged position and a released position, thereby releasing the collar to impact the head of the rod, causing an extraction force.

2. The impact tool of claim 1 wherein the first diameter is larger than the second diameter.

3. The impact tool of claim 1 wherein the collar has a shoulder and wherein the return spring engages the shoulder of the collar.

4. The impact tool of claim 1 wherein the head of the rod has a shoulder and wherein an end of the return spring is positioned against the shoulder.

5. The impact tool of claim 1 wherein the calibration knob is threadably connected to the second end of the body.

6. The impact tool of claim 5 wherein said calibration knob has a shoulder, an end of the impact spring is positioned against the shoulder.

7. The impact tool of claim 1 wherein the head is threadably attached to the first end of the rod.

8. The impact tool of claim 1 wherein:

the collar has a hole formed through a wall thereof, the hole extending through the wall of the collar, perpendicular to the opening in the collar, and into an inner surface thereof, such that a depression is formed in the inner surface of the collar aligned with the hole, the rod has a boss formed thereon, and the trigger has an actuation spring secured in the depression and a trigger member slidably retained in the hole and pressing against the spring, the trigger member having a bottom surface and an opening disposed therethrough perpendicular to the bottom surface to form a bottom edge, the opening in the trigger dimensioned to allow the rod to extend through the trigger and into the cavity, the actuation spring biasing the trigger member outwardly, such that a head of the trigger normally projects outwardly from the periphery of the collar, wherein as the collar is moved toward the second end of the body, the head of the trigger contacts the transition portion of the body, as the collar moves through the transition portion, the trigger member compresses the actuation spring until the trigger member disengages from the boss in the rod, allowing the collar to move, whereupon the collar is impelled by the impact spring to strike the head of the rod, creating the extraction force, and wherein, when the impact tool is released, the impact spring and return springs reset the impact tool by moving the collar and the rod towards the first end of the body, allowing the actuation spring to push the trigger back into the boss in the rod.

9. The impact tool of claim 1 wherein the impact spring and the return spring are compression springs.

10. The impact tool of claim 1 further comprising a quick-disconnect assembly releasably connecting the grasping implement to the rod.

11. The tool of claim 1 wherein the impact tool is formed from a biocompatible material.

12. The impact tool of claim 1 wherein the calibration knob has a multiplicity of spatially positioned elongated furrows in the periphery thereof.

13. An impact tool for use with an extraction implement, the impact tool comprising:

a body having a first end, a second end, and an opening extending therethrough, the opening having a first diameter at the first end, a second, smaller diameter at the second end, and a transition portion which tapers between said first and second diameters, a calibration knob having a shoulder, the calibration knob being connected with the second end of the body, a rod having a first end and a second end, the first end of the rod being located within the body, the second end of the rod being configured to connect with the extraction implement, a head extending around the edge of the first end of the rod, the head having a shoulder extending around the perimeter thereof, a collar located within the body and slidably engaging the rod between the first and second ends thereof and slidably engaging the body, the collar having a shoulder, a trigger extending through the collar, an impact compression spring positioned between the shoulder of the collar and the shoulder of the calibration knob, the impact spring biasing the collar towards the first end of the body, and a return compression spring positioned between the shoulder of the head of the rod and the collar, the return spring biasing the head of the rod away from the collar, wherein, when the extraction implement is engaged with an object to be pulled and the body of the impact tool is pulled, the collar is moved within the opening of the body between the first and second diameters, causing the trigger to move between an engaged position and a released position, thereby releasing the collar to impact the head of the rod, causing an extraction force.

14. The impact tool of claim 13 wherein the calibration knob is threadably connected to the second end of the body.

15. The impact tool of claim 13 wherein the head is threadably attached to the first end of the rod.

16. The impact tool of claim 13 wherein:

the collar has a hole formed through a wall thereof, the hole extending through the wall of the collar, perpendicular to the opening in the collar, and into an inner surface thereof, such that a depression is formed in the inner surface of the collar aligned with the hole, the rod has a boss formed thereon, and the trigger has an actuation spring secured in the depression and a trigger member slidably retained in the hole and pressing against the spring, the trigger member having a bottom surface and an opening disposed therethrough perpendicular to the bottom surface to form a bottom edge, the opening in the trigger dimensioned to allow the rod to extend through the trigger and into the cavity, the actuation spring biasing the trigger member outwardly, such that a head of the trigger normally projects outwardly from the periphery of the collar, wherein as the collar is moved toward the second end of the body, the head of the trigger contacts the transition portion of the body, as the collar moves through the transition portion, the trigger member compresses the actuation spring until the trigger member disengages from the boss in the rod, allowing the collar to move, whereupon the collar is impelled by the impact spring to strike the head of the rod, creating the extraction force, and wherein when the impact tool is released, the impact spring and return springs reset the impact tool by moving the collar and the rod towards the first end of the body, allowing the actuation spring to push the trigger back into the boss in the rod.

17. The impact tool of claim 13 further comprising a quick-disconnect assembly releasably connecting the grasping implement to the rod.

18. The tool of claim 13 wherein the impact tool is formed from a biocompatible material.

* * * * *